United States Patent
Xie et al.

(10) Patent No.: US 8,309,602 B2
(45) Date of Patent: Nov. 13, 2012

(54) MULTI-SUBSTITUTED DIARYLANILINES AS NON-NUCLEOSIDE HIV REVERSE TRANSCRIPTASE INHIBITORS, AND PREPARATION AND USE THEREOF

(75) Inventors: Lan Xie, Beijing (CN); Bingjie Qin, Beijing (CN); Kuo-Hsiung Lee, Chapel Hill, NC (US); Shibo Jiang, Fresh Meadows, NY (US); Hong Lu, Bayside, NY (US)

(73) Assignees: Institute of Pharmacology and Toxicology, Beijing (CN); Academy of Military Medical Sciences P.L.A. China, Beijing (CN)

( * ) Notice: Subject to any disclaimer, the term of this patent is extended or adjusted under 35 U.S.C. 154(b) by 225 days.

(21) Appl. No.: 12/682,513

(22) PCT Filed: Oct. 7, 2008

(86) PCT No.: PCT/CN2008/001699
§ 371 (c)(1),
(2), (4) Date: May 4, 2010

(87) PCT Pub. No.: WO2009/049491
PCT Pub. Date: Apr. 23, 2009

(65) Prior Publication Data
US 2010/0292324 A1    Nov. 18, 2010

(30) Foreign Application Priority Data
Oct. 12, 2007    (CN) .......................... 2007 1 0163958

(51) Int. Cl.
*A61K 31/277* (2006.01)
*A61K 31/136* (2006.01)
*C07C 255/50* (2006.01)
*C07C 255/51* (2006.01)
*C07C 211/46* (2006.01)

(52) U.S. Cl. ........ 514/524; 514/525; 514/658; 558/418; 558/420; 564/441

(58) Field of Classification Search .................. 514/524, 514/525, 658; 558/418, 420; 564/441
See application file for complete search history.

(56) References Cited

U.S. PATENT DOCUMENTS
2005/0239881 A1    10/2005    Dunn et al.

FOREIGN PATENT DOCUMENTS
| CN | 1494528 | A  | 5/2004 |
| CN | 1541215 | A  | 10/2004 |
| CN | 1946680 | A  | 4/2007 |
| WO | 02070470 | A2 | 12/2002 |
| WO | 03016306 | A1 | 2/2003 |

*Primary Examiner* — Kristin Bianchi
(74) *Attorney, Agent, or Firm* — The Webb Law Firm

(57) ABSTRACT

The present invention relates to multi-substituted m-diarylanilines or pharmaceutically acceptable salts thereof, wherein X, $R_1$-$R_7$ are as defined in the claims, their preparation process, pharmaceutical compositions comprising them and their use for the manufacture of a medicament for anti-HIV.

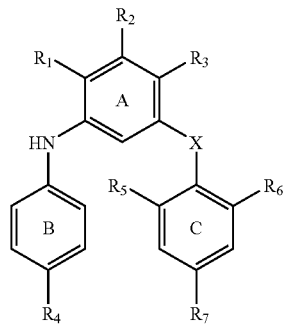

11 Claims, No Drawings

MULTI-SUBSTITUTED DIARYLANILINES AS NON-NUCLEOSIDE HIV REVERSE TRANSCRIPTASE INHIBITORS, AND PREPARATION AND USE THEREOF

FIELD OF THE INVENTION

The invention relates to a class of multi-substituted m-diarylaniline derivatives with anti-HIV activity, its preparation process, a pharmaceutical composition comprising the same, and their use for the manufacture of a medicament for anti-HIV.

BACKGROUND OF THE INVENTION

Human immunodeficiency virus (HIV) is a RNA virus. The surface of this virus is a layer of double lipid membrane. The membrane encapsulates 2 single chain RNA and some important enzymes (e.g. reverse transcriptase, protease, integrase) and structural protein (p24, p17, p7, etc). The membrane surface of the virus has two very important glycoproteins gp120 and gp41. The gp120 is outside of the membrane, gp41 bestrides the double lipid membrane and forms a composite with gp120. Their main function is to recognize and attack cells having CD4 surface receptors in human immune system, such as lymphocyte (T cell), macrophage. HIV cannot be propagated in vitro, it can be replicated and regenerated only by means of human cells. The replication course of HIV can be approximately divided into following stages: binding and fusing of virus and host cells, reverse transcription of virus genes, integration, transcription and translation, and assembly and release of virus. HIV continuously replicates in such a circulation course, infects human immune cells, destroys human immune system, and finally causes the complete loss of human immune function, so that patients are placed in the risk of various infections without resistance ability. Theoretically, only if a drug can interrupt any link during the replication of virus, the purpose of inhibiting virus and treating diseases can be achieved.

Up to now, there are 30 kinds of chemical drugs and their combinations that have been approved to be marketed for clinic anti-HIV infection and treating AIDS. Existing drugs are divided into five classes in terms of action mechanism: nucleoside reverse transcriptase inhibitors (NRTIs), non-nucleoside reverse transcriptase inhibitors (NNRTIs), protease inhibitors (PIs), fusion inhibitors (Enfuvirtide), and entrance inhibitors (Maraviroc). The use of existing drugs alone or in combination can effectively inhibit the replication of virus, however, the main problem commonly faced is drug resistance. HIV viruses may exhibit some mutation after interacting with drugs. Mutated virus cannot be inhibited by drugs, and still continuously replicates a great deal of virus in vivo as before drug administration. Therefore, seeking and developing a new generation of anti-HIV drugs having new structure type, new action mechanism, new action target or exhibiting strong inhibition effect on virus having drug resistance has been recently a focus in drug study field.

At present, there are only three public listed non-nucleoside reverse transcriptase inhibitors (Nevirapine, Delavirdine, Efavirenz). These drugs have advantages of structural diversity, high efficiency and low toxicity, clear target and action mechanism as well as non-competitive inhibitors, and occupy important places in anti HIV combination therapy (HAART). However, their main problem is to cause drug resistance easily. In order to overcome the disadvantages of the existing drugs, it is needed to seek a new generation of non-nucleoside reverse transcriptase inhibitors drugs which can effectively inhibit the replication of wild type and multiple drug resistance HIV virus strains.

SUMMARY OF THE INVENTION

The inventor has found in the study of new anti-HIV drugs that a class of compounds having novel structure have rather strong anti-HIV activity and may be developed to be new anti-HIV drugs.

Therefore, the present invention relates to, at first aspect, a compound of multi-substituted m-diarylanilines represented by formula (I) or a pharmaceutically acceptable salt thereof:

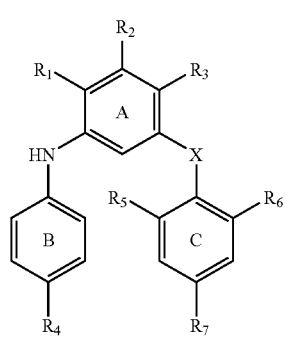

I wherein,
$R_1$, $R_2$ and $R_3$ are each independently —H, halogen, —$NO_2$, —$NH_2$, —NHR, —$N(R)_2$, —CN, —OH, $C_{1-6}$alkyl, $C_{1-6}$alkoxy, —$CF_3$, —COOH, —$SO_3H$, —$CONH_2$, —CONHR' or —COOR',
or, $R_1$ and $R_2$ or $R_2$ and $R_3$ can form together —$OCH_2O$—;
$R_4$ is —CN, —CH=$CH_2$, —C≡CH, $C_{1-6}$alkoxy, —$CF_3$, halogen, —$NH_2$, —OH, —COOH, —$SO_3H$, —C≡CR' or —CH=CHR';
$R_5$ and $R_6$ are each independently halogen, $C_{1-6}$alkyl, $C_{1-6}$alkoxy, —$CF_3$, —$NH_2$, —OH, —COOH, —$SO_3H$ or —COOR';
$R_7$ is —CN, —HC=CH—CN, halogen, $C_{1-6}$alkyl, $C_{1-6}$alkoxy, —$NH_2$, —OH, —$NO_2$, —$CF_3$, —CH=$CH_2$, —C≡CR', —CH=CHR', —CH=CHCOR', —CHO, 5-membered heteroaryl containing 1-3 heteroatoms selected from N, O and S, and optionally having on the ring structure thereof aldehyde, ketone, cyano, α,β-unsaturated cyano, alkenyl, alkynyl, aldehyde or ketone group substitution;
R' is H or $C_{1-6}$alkyl radical;
X: —NH—, —O—, —S—, —$CH_2$—, —CO—, —CHOH—, —CHOR—, —NR—, —NCOR—; and
R is $C_{1-4}$alkyl radical.

The present invention relates to, at second aspect, a process for preparing a compound of formula (I) or a pharmaceutically acceptable salt thereof.

The present invention relates to, at third aspect, a pharmaceutical composition comprising at least one compound of formula (I) or a pharmaceutically acceptable salt thereof and one or more pharmaceutically acceptable carriers or excipients.

The present invention relates to, at fourth aspect, a use of a compound of formula (I) or a pharmaceutically acceptable salt thereof for the manufacture of a medicament for treating HIV infection associated diseases or disorders.

DETAILED DESCRIPTION OF THE INVENTION

The term "alkyl radical" used in the present invention includes alkyl, alkenyl and alkynyl.

The term "5-membered heteroaryl" used in the present invention means 5-membered heteroaromatic ring system containing 1-3 heteroatoms selected O, S or N, including but not being limited to furyl, pyrrolyl, thienyl, pyrazolyl, etc.

The term "5-membered heteroaryl having on the ring structure thereof aldehyde, ketone, cyano, α,β-unsaturated cyano, alkenyl, alkynyl, aldehyde or ketone group substitution" mentioned in the present invention can be shown as follows, including but not being limited to:

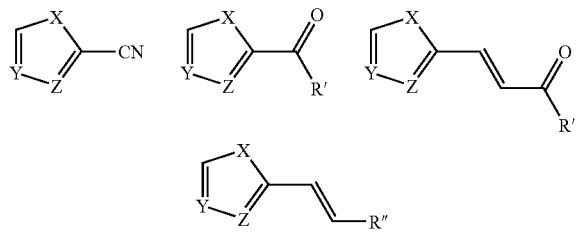

R' is H, $C_{1-6}$alkyl radical;
R'' is H, —CN, $C_{1-4}$alkyl radical;
X, Y and Z each independently represent heteroatoms selected from N, O, S or are carbon atom.

According to one embodiment of the present invention, the present invention relates to a compound of formula (I) shown as follows:

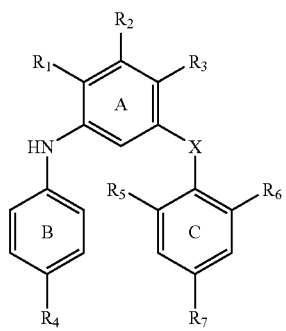

I wherein,
$R_1$, $R_2$ and $R_3$ are each independently —H, halogen, —NO$_2$, —NH$_2$, —NHR, —N(R)$_2$, —CN, —OH, $C_{1-6}$alkyl, $C_{1-6}$alkoxy, —CF$_3$, —COOH, —SO$_3$H, —CONH$_2$, —CONHR' or —COOR',
or, $R_1$ and $R_2$ or $R_2$ and $R_3$ can form together —OCH$_2$O—;
$R_4$ is —CN, —CH=CH$_2$, —C≡CH, $C_{1-6}$alkyl, $C_{1-6}$alkoxy, —CF$_3$, halogen, —NH$_2$, —OH, —COOH, —SO$_3$H, —C≡CR' or —CH=CHR';
$R_5$ and $R_6$ are each independently halogen, $C_{1-6}$alkyl, $C_{1-6}$alkoxy, —CF$_3$, —NH$_2$, —OH, —COOH, —SO$_3$H or —COOR';
$R_7$ is —CN, —HC=CH—CN, halogen, $C_{1-6}$alkyl, $C_{1-6}$alkoxy, —NH$_2$, —OH, —NO$_2$, —CF$_3$, —CH=CH$_2$, —C≡CR', —CH=CHR', —CH=CHCOR', —CHO, 5-membered heteroaryl containing 1-3 heteroatoms selected from N, O and S, and optionally having on the ring structure thereof aldehyde, ketone, cyano, α,β-unsaturated cyano, alkenyl, alkynyl, aldehyde or ketone group substitution;
R' is H or $C_{1-6}$alkyl radical;
X: —NH—, —O—, —S—, —CH$_2$—, —CO—, —CHOH—, —CHOR—, —NR—, —NCOR—; and
R is $C_{1-4}$alkyl radical.

According to one preferred embodiment of the present invention, X is —O—.

According to one preferred embodiment of the present invention, the compound of formula (I) of the present invention has following formula (Ia):

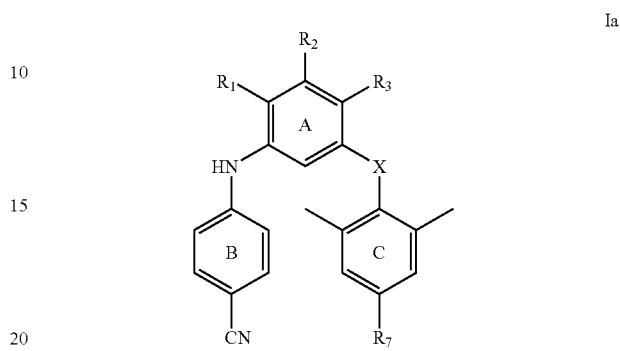

Ia wherein,
$R_1$ and $R_3$ are each independently —NO$_2$, —NH$_2$, halogen, —OH, —CN or —N(R)$_2$;
$R_2$—H;
$R_7$ is —CN, —HC=CH—CN, halogen, —CH$_3$, —OCH$_3$, —NH$_2$, —OH, —NO$_2$, —CF$_3$, —CH=CH$_2$, —C≡CH, —C≡CR', —CH=CHR', —CH=CHCOR', —CHO, 5-membered heteroaryl containing 1-3 heteroatoms selected from N, O and S, and optionally having on the ring structure thereof aldehyde, ketone, cyano, α,β-unsaturated cyano, alkenyl, alkynyl, aldehyde or ketone group substitution;
R' is H or $C_{1-6}$alkyl radical;
X is —O—, —NH— or —NCOR—; and
R is $C_{1-4}$alkyl radical.

According to another preferred embodiment of the present invention, the compound of formula (I) of the present invention has following formula (Ia), wherein
$R_1$ is —NO$_2$, —NH$_2$, halogen, —OH, —CN or —N(R)$_2$;
$R_2$ and $R_3$ are —H;
$R_7$ is —CN, —HC=CH—CN, halogen, —CH$_3$, —OCH$_3$, —NH$_2$, —OH, —NO$_2$, —CF$_3$, —CH=CH$_2$, —C≡CH, —C≡CR', —CH=CHR', —CH=CHCOR', —CHO, 5-membered heteroaryl containing 1-3 heteroatoms selected from N, O and S, and optionally having on the ring structure thereof aldehyde, ketone, cyano, α,β-unsaturated cyano, alkenyl, alkynyl, aldehyde or ketone group substitution;
R' is H or $C_{1-6}$alkyl radical;
X is —O—, —NH— or —NCOR—; and
R is $C_{1-4}$alkyl radical.

According to another preferred embodiment of the present invention, the compound of formula (I) of the present invention has following formula (Ia), wherein
$R_2$ is —NO$_2$, —NH$_2$, halogen, —OH, —CN or —N(R)$_2$;
$R_1$ and $R_3$ are —H;
$R_7$ is —CN, —HC=CH—CN, halogen, —CH$_3$, —OCH$_3$, —NH$_2$, —OH, —NO$_2$, —CF$_3$, —CH=CH$_2$, —C≡CH, —C≡CR', —CH=CHR', —CH=CHCOR', —CHO, 5-membered heteroaryl containing 1-3 heteroatoms selected from N, O and S, and optionally having on the ring structure thereof aldehyde, ketone, cyano, α,β-unsaturated cyano, alkenyl, alkynyl, aldehyde or ketone group substitution;
R' is H or $C_{1-6}$alkyl radical;
X is —O—, —NH— or —NCOR—; and
R is $C_{1-4}$alkyl radical.

According to another preferred embodiment of the present invention, the compound of formula (I) of the present invention has following formula (Ia), wherein
$R_3$ is —$NO_2$, —$NH_2$, halogen, —OH, —CN or —$N(R)_2$;
$R_1$ and $R_2$ are H;
$R_7$ is —CN, —HC=CH—CN, halogen, —$CH_3$, —$OCH_3$, —$NH_2$, —OH, —$NO_2$, —$CF_3$, —CH=$CH_2$, —C≡CH, —C≡CR', —CH=CHR', —CH=CHCOR', —CHO, 5-membered heteroaryl containing 1-3 heteroatoms selected from N, O and S, and optionally having on the ring structure thereof aldehyde, ketone, cyano, α,β-unsaturated cyano, alkenyl, alkynyl, aldehyde or ketone group substitution;
R' is H or $C_{1-6}$alkyl radical;
X is —O—, —NH— or —NCOR—; and
R is $C_{1-4}$alkyl radical.

According to another preferred embodiment of the present invention, the compound of formula (I) of the present invention has following formula (Ia), wherein
$R_3$ is —$NO_2$, —$NH_2$, halogen, —OH, —CN or —$N(R)_2$;
$R_1$ and $R_2$ are H;
$R_7$ is —CN, —HC=CH—CN, halogen, —$CH_3$, —$OCH_3$, —$NH_2$, —OH, —$NO_2$, —$CF_3$, —CH=$CH_2$, —C≡CH, —C≡CR', —CH=CHR', —CH=CHCOR', —CHO, 5-membered heteroaryl containing 1-3 heteroatoms selected from N, O and S, and optionally having on the ring structure thereof aldehyde, ketone, cyano, α,β-unsaturated cyano, alkenyl, alkynyl, aldehyde or ketone group substitution;
R' is H or $C_{1-6}$alkyl radical;
X is —O— or —NH—; and
R is $C_{1-4}$alkyl radical.

According to another preferred embodiment of the present invention, the compound of formula (I) of the present invention has formula (Ia) said above, wherein
$R_1$ and $R_2$ or $R_2$ and $R_3$ together represent —$OCH_2O$—, the remaining $R_3$ or $R_1$ is H, —OH, —$NH_2$, —$NO_2$ or halogen;
$R_7$ is —CN, —HC=CH—CN, halogen, —$CH_3$, —$OCH_3$, —$NH_2$, —OH, —$NO_2$, —$CF_3$, —CH=$CH_2$, —C≡CR', —CH=CHR', —CH=CHCOR', —CHO, 5-membered heteroaryl containing 1-3 heteroatoms selected from N, O and S, and optionally having on the ring structure thereof aldehyde, ketone, cyano, α,β-unsaturated cyano, alkenyl, alkynyl, aldehyde or ketone group substitution;
R' is H or $C_{1-6}$alkyl radical;
X is —O—, —S—, —$CH_2$—, —NH—, —NCOR—; and
R is $C_{1-4}$alkyl radical.

Following compounds are more preferred in the present invention:
$N^1$-(4'-cyanophenyl)-5-(2',6'-dimethyl-4'-bromophenoxy)-2,4-dinitroaniline;
$N^1$-(4'-cyanophenyl)-5-(2',6'-dimethylphenoxy)-2,4-dinitroaniline;
$N^1$-(4'-cyanophenyl)-2,4-dinitro-$N^5$-(2',4',6'-trimethylphenyl)-benzene-1,5-diamine;
$N^1$-(4'-cyanophenyl)-2,4-dinitro-[$N^5$-N-acetoxy-$N^5$-(2',4',6'-trimethylphenyl)]-benzene-1,5-diamine;
4-(4'-bromo-2',6'-dimethylphenoxy)-$N^2$-(4'-cyanophenyl)-5-nitrobenzene-1,2-diamine;
$N^1$-(4'-cyanophenyl)-5-(4'-cyano-2',6'-dimethylphenoxy)-2-nitroaniline;
$N^1$-(4'-cyanophenyl)-5-(2',6'-dimethylphenoxy)-2-nitroaniline;
5-(4'-bromo-2',6'-dimethylphenoxy)-$N^1$-(4'-cyanophenyl) benzene-1,2,4-triamine;
$N^1$-(4'-cyanophenyl)-5-(4'-cyano-2',6'-dimethylphenoxy)-2,4-dinitroaniline;
$N^1$-(4'-cyanophenyl)-5-(4'-cyano-2',6'-dimethylphenoxy) benzene-1,2,4-triamine;
5-(4'-cyano-2',6'-dimethylphenoxy)-$N^1$-(4'-cyanophenyl)-4-nitrobenzene-1,2-diamine;
5-(4'-bromo-2',6'-dimethylphenoxy)-$N^1$-(4'-cyanophenyl)-2-nitroaniline;
4-(4'-bromo-2',6'-dimethylphenoxy)-$N^2$-(4'-cyanophenyl)-benzene-1,2-diamine;
$N^1$-(4'-cyanophenyl)-5-(2',4'6'-trimethylphenoxy)-2,4-dinitroaniline,
5-(2',6'-dimethylphenoxy)-2,4-dinitro-$N^1$-(4'-methylphenyl) aniline;
5-(4'-bromo-2',6'-dimethylphenoxy)-2,4-dinitro-$N^1$-(4'-methylphenoxy)aniline;
$N^1$-(4'-cyanophenyl)-5-(2',6'-dimethylphenoxy)-3-nitroaniline;
$N^1$-(4'-cyanophenyl)-5-(4'-propenylcyano-2',6'-dimethylphenoxy)-2,4-dinitroaniline;
$N^1$-(4'-cyanophenyl)-5-(4'-propenylcyano-2',6'-dimethylphenoxy)-4-nitrobenzene-1,2-diamine; and
$N^1$-(4'-Cyanophenyl)-5-{2',6'-dimethyl-4'-[2''-(5''-formylfuran)]phenoxy}-2,4-dinitroaniline.

The compounds of the present invention can be prepared through following reaction routes:

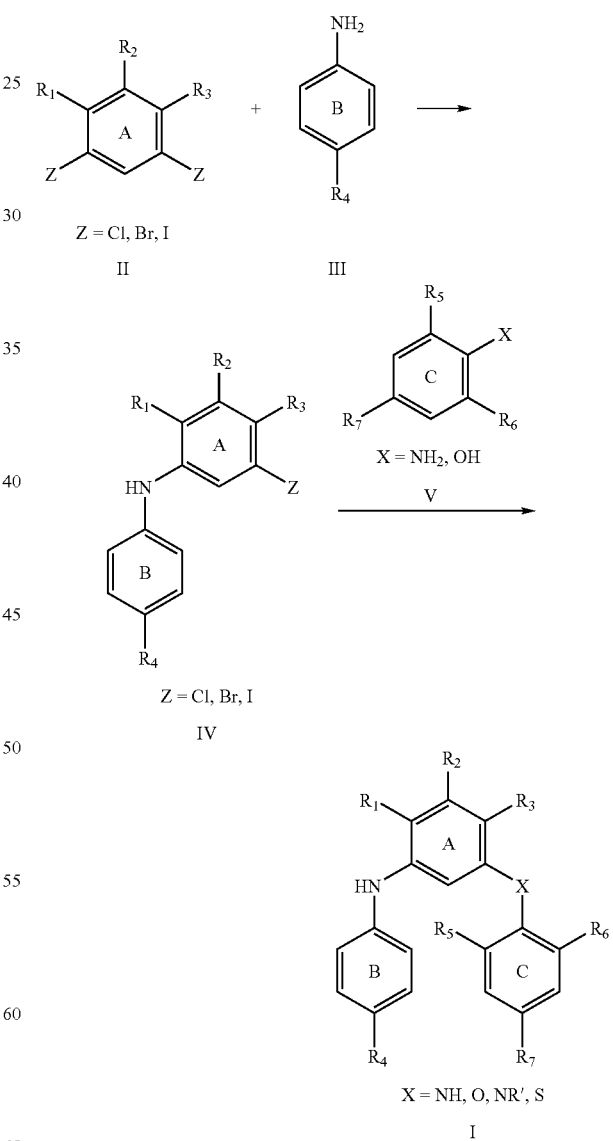

wherein $R_1$-$R_7$ and X are as defined in the formula (I).

Substituted m-dihalobenzene of formula (II) is allowed to react with p-substituted anilines in the presence of a strong base to form N-aryl substituted aniline, i.e. intermediate of formula (IV); then the intermediate of formula (IV) and multi-substituted phenols or anilines are subjected to coupling reaction, or heated in the presence of Pd catalyst or coupled under microwave condition to produce the target compound of multi-substituted m-diarylanilines as shown in formula (I).

Besides, a part of the target compounds of formula (I) are obtained by two-step coupling reaction simultaneously under microwave reaction condition, i.e. "one pot reaction".

For example, the compound of formula (Ia) according to the present invention can be prepared by following synthetic routes:

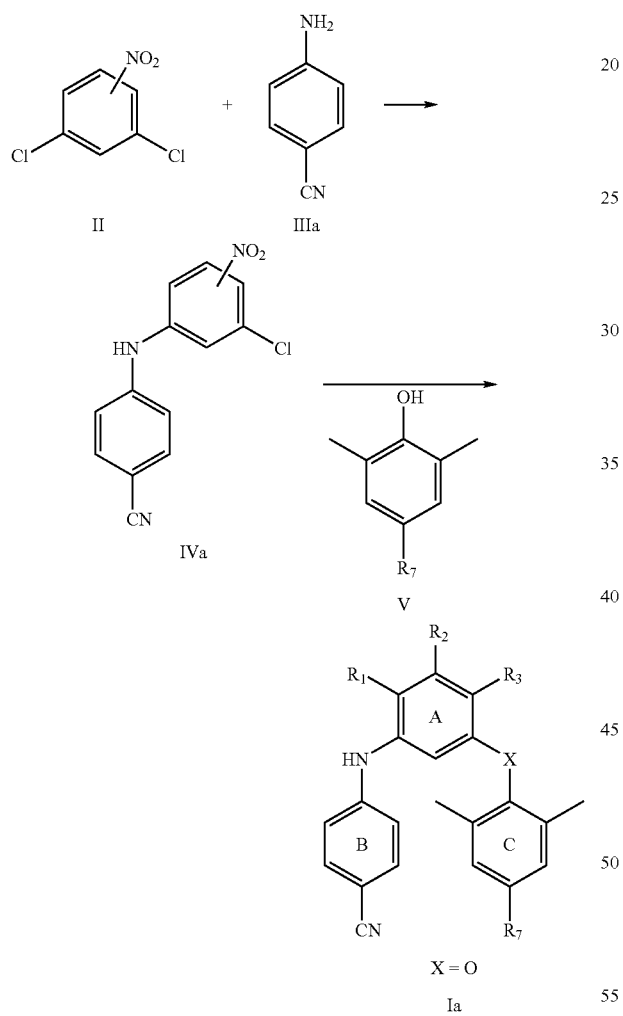

wherein, $R_1$, $R_2$, $R_3$ and $R_7$ are as defined in the formula (I); the compound of formula (II) having appropriate $R_1$, $R_2$, $R_3$ substituents can be selected as starting materials based on requirements.

Arylamine Coupling Synthesis of Intermediate of Formula (IV)

Particularly, m-dihalo-nitrobenzene (II) and p-substituted aniline or substituted phenol (formula IIIa) are allowed to react at a temperature of between room temperature and 130° C. for from 5 minutes to 24 hours in the presence of potassium tert-butoxide, sodium hydride, triethylamine, pyridine, N,N-dimethylaminopyridine, or potassium carbonate/cuprous halide (I) in a solvent of DMF, acetonitrile, THF or DMSO to give N-(p-substituted aryl) aniline or phenylate intermediate (IVa). The molar ratio of reactant II/III is 1:1.1-1:2.

This coupling reaction can also be carried out at a temperature of 150-180° C. under microwave condition in a solvent of DMF or DMSO for 10-30 minutes to give an intermediate (IV-a). The molar ratio of base to reactant is as defined above.

Synthesis of Target Compound (I)

For example, when X in the formula is —O—, its synthetic method is as follows:

Method 1: N-aryl-m-chloroaniline (formula IV-a) and multi-substituted phenol (formula V) are heated in an atmosphere of nitrogen to 130° C. and allowed to react in the presence of Cu or cuprous reagent (e.g. CuI, CuBr) catalyst and $K_2CO_3$ in a solvent of DMSO, DMF for about 4 hours.

Method 2: In dried ethyl ether, tri-substituted phenol of formula V is allowed to react with NaH to form sodium salt, and then the sodium salt and N-aryl-m-chloroaniline of formula (IV-a) are refluxed in DMF for 0.5-8 hours.

Method 3: The intermediate of formula (IV-a) is allowed to react with sodium phenolate or potassium phenolate under microwave condition for 5-10 minutes.

Method 4: The intermediate of formula (IV-a) is allowed to react with substituted phenol (formula V) and potassium carbonate under microwave condition in a solvent of DMSO for 5-10 minutes.

Also, for example, when the X in the target compound formula is —NH—, its synthetic method is as follows:

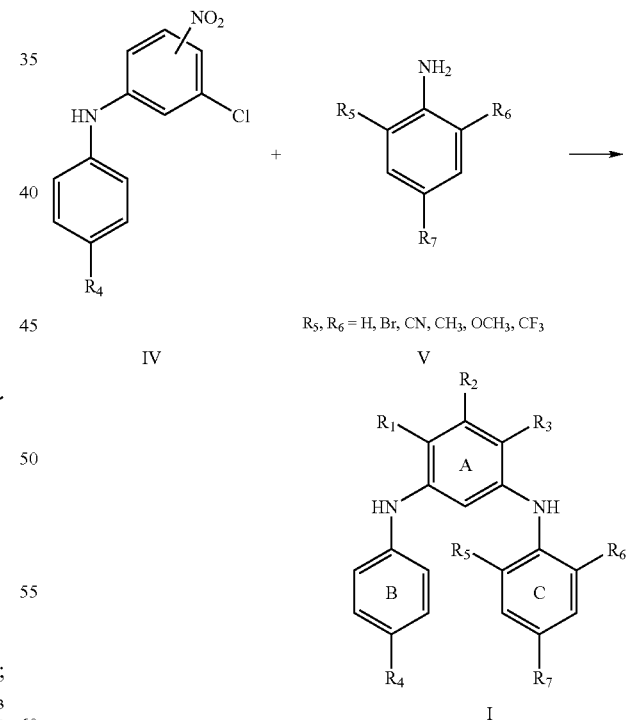

wherein each substituent is as defined in the formula (I); the compound of formula (IV) having appropriate $R_1$, $R_2$, $R_3$ substituents can be selected as starting materials based on requirements.

Method 5: The intermediate chlorobenzene of formula (IV) is allowed to react with substituted aniline of formula (VI) at 140-160° C. in an atmosphere of nitrogen in the presence of Cu, CuI or CuBr catalyst and $K_2CO_3$ in an aprotic polar solvent (e.g. DMSO or DMF) for about 6 hours.

Method 6: The intermediate chlorobenzene of formula (IV) is allowed to react with substituted aniline of formula (VI) at about 100° C. in an atmosphere of nitrogen in the presence of Pd catalyst and $Cs_2CO_3$ in toluene solvent for 1-20 hours.

Method 7: If the arylamine of formula (VI) is liquid, no other solvent is required, the arylamine of formula (VI) can be directly mixed with the intermediate of formula (IV) and allowed to react at the boiling point temperature of arylamine under microwave for about 15-20 minutes.

Method 8: The arylamine of formula (VI) is allowed to react with the intermediate chlorobenzene of formula (IV) at a molar ratio of 4:1 at a temperature of 200-250° C. under microwave in the presence of potassium tert-butoxide in DMSO or NMP solvent for 15-20 minutes.

Similarly, the compound of formula (I) wherein X has other definitions can be prepared too.

The multi-substituted m-diarylanilines shown in formula (I) according to the present invention exhibit strong anti-HIV activity and high selectivity in the cell experiments of inhibiting HIV replication (MT-2 and H9 lymphocyte). Hence, further study on the compounds of the present invention is helpful to develop new anti-HIV drugs.

The compounds of the present invention can be used in the form of the compounds themselves or pharmaceutically acceptable salts or solvates thereof. The pharmaceutically acceptable salts of the compounds of formula (I) include customary salts formed with pharmaceutically acceptable inorganic acids or organic acids, or inorganic bases or organic bases. The examples of suitable acid addition salts include the salts formed with hydrochloric acid, hydrobromic acid, sulfuric acid, phosphoric acid, nitric acid, perchloric acid, fumaric acid, acetic acid, propionic acid, succinic acid, glycolic acid, formic acid, lactic acid, maleic acid, tartaric acid, citric acid, embonic acid, malonic acid, hydroxymaleic acid, phenylacetic acid, glutamic acid, benzoic acid, salicylic acid, fumaric acid, tosylic acid, mesylic acid, naphthalene-2-sulfonic acid, benzenesulfonic acid, hydroxynaphthoic acid, hydroiodic acid, malic acid, tannic acid. The examples of suitable base addition salts include the salts foamed with sodium, lithium, potassium, magnesium, aluminium, calcium, zinc, N,N'-dibenzylethylenediamine, procaine chloride, choline, diethanolamine, ethylenediamine, N-methylglucosamine and procaine. When the compounds of the present invention are mentioned in the present invention, they include compounds of formula (I) and pharmaceutically acceptable salts or solvates thereof.

According to the present invention, the compounds of formula (I) of the present invention can faun pharmaceutical compositions with pharmaceutically acceptable customary carriers and excipients. The pharmaceutical compositions can be administered orally or non-intestinally. The pharmaceutical composition of the present invention can be prepared by conventional methods in this art into various dosage forms, including but being not limited to: tablets, capsules, solutions or suspensions, granulates or injections, which are administered orally non-intestinally.

Further, it should be pointed out that the application dosage and application method of the compounds of the present invention depend on various factors, including age, body weight, sex, natural health condition and nutrition state of patients, the activity of the compounds applied, administration time, metabolism rate, order of severity of conditions and doctor's subjective judgment. The application dosage is preferably between 0.01 and 100 mg/kg body weight/day.

EXAMPLES

Following examples are used to further explain the present invention. However, the present invention is not limited by the examples at any way.

Preparation Example 1

5-Chloro-$N^1$-(4'-cyanophenyl)-2,4-dinitroaniline (IV-1)

2,4-Dichloro-1,5-dinitrobenzene (II-1, 1.2 g, 5 mmol) and p-cyanoaniline (III-1, 0.59 g, 5 mmol) were dissolved in N,N-dimethylformamide (DFM, 10 ml). To the solution was added potassium tert-butoxide (1.4 g, 12.5 mmol) in batches in ice water bath. The mixture was allowed to react at room temperature for 45 minutes. The reaction liquid was poured into ice water. The pH value was adjusted to about 6 with dilute hydrochloric acid. The mixture was stirred for 30 minutes to precipitate a solid. The solid was filtered, washed with water to neutrality, dried, and separated on silica gel column (eluted with ethyl acetate: petroleum ether) to obtain a compound VI-1 (1.44 g, faint yellow solid). $^1$H NMR (CDCl$_3$) δ ppm 7.41 (1H, s, ArH-6), 7.57 (2H, d, J=8.7 Hz, ArH-3', 5'), 7.91 (2H, d, J=8.7 Hz, ArH-2', 6'), 8.90 (1H, s, ArH-3), 10.07 (1H, s, NH).

Preparation Example 2

5-Chloro-2,4-dinitro-N-(4'-methoxyphenyl)aniline (IV-2)

2,4-Dichloro-1,5-dinitrobenzene (II-1, 0.5 g, 2.11 mmol) and p-methoxyaniline (III-2, 0.2 g, 2.11 mmol) were dissolved in 5 mL DMSO. To the solution were added $K_2CO_3$ (0.58 g, 4.22 mmol) and metal Cu in catalytic amount. The mixture was allowed to react at 115° C. for 2 hours with stirring in an atmosphere of nitrogen. The resultant was poured into ice water, stirred to precipitate a solid. The solid was filtered, washed with water several times, dried, and separated on silica gel column (petroleum ether/ethyl acetate) to obtain a bronzing solid (IV-2, 0.68 g, 67%). $^1$H NMR (CDCl$_3$) δ ppm 3.88 (3H, s, OCH$_3$), 7.02 (1H, s, ArH-6), 7.03 (2H, d, J=8.96 Hz, ArH-3', 5'), 7.21 (2H, d, J=8.96 Hz, ArH-2', 6'), 9.07 (1H, s, ArH-3), 9.73 (1H, s, NH).

Preparation Example 3

5-Chloro-2,4-dinitro-N-(4'-methylphenyl)-aniline (IV-3)

The preparation method was the same as described in the preparation of IV-2, yield 70%. $^1$H NMR δ ppm 2.08 (3H, s, CH$_3$), 6.86 (2H, d, J=8.12 Hz, ArH-3', 5'), 7.03 (1H, s, ArH-6), 7.10 (2H, d, J=8.12 Hz, ArH-2', 6'), 9.16 (1H, s, ArH-3), 9.71 (1H, s, NH).

Preparation Example 4

5-Chloro-$N^1$-(4'-cyanophenyl)-2-nitroaniline (IV-4)

The preparation method was the same as described in the preparation of IV-1, yield 63%. $^1$H NMR (CDCl$_3$) δ ppm 7.17 (1H, d, J=8.9 Hz, ArH-5), 7.40 (2H, d, J=8.7 Hz, ArH-2', 6'), 7.45 (1H, s, ArH-3), 7.79 (2H, d, J=8.7 Hz, ArH-3', 5'), 8.14 (1H, d, J=8.9 Hz, ArH-6), 9.49 (1H, s, NH).

Preparation Example 5

5-Chloro-N-(4'-cyanophenyl)-3-nitroaniline (IV-5)

The preparation method was the same as described in the preparation of IV-1, yield 50%. $^1$H NMR (CDCl$_3$) δ ppm 6.25 (1H, s, ArH-6), 6.78 (2H, d, J=8.68 Hz, ArH-3', 5'), 7.55 (2H, d, J=8.68 Hz, ArH-2', 6'), 7.83 (1H, s, ArH-2), 8.02 (1H, s, ArH-4).

Example 1

$N^1$-(4'-cyanophenyl)-5-(2',6'-dimethyl-4'-bromophenoxy)-2,4-dinitroaniline (I-1)

Compound IV-1 (318 mg, 1 mmol) and 4-bromo-2,6-dimethylphenol (242 mg, 1.2 mmol) were dissolved in DMSO (2 mL). To the solution were added K$_2$CO$_3$ (276 mg, 2 mmol), allowed to react at 192° C. under microwave for 15 minutes. The resultant was poured into ice-water, the pH value was adjusted to neutrality with dilute hydrochloric acid, stirred for half an hour. The resulting solid was filtered, washed with water, dried, and separated on silica gel column to obtain a faint yellow compound I-1 (410 mg, 85%). Mass spectrum (EI-MS): m/z (%) 483 [M$^+$, 100]; $^1$H NMR (DMSO-d$_6$) δ ppm 2.05 (6H, s, 2×CH$_3$), 5.93 (1H, s, ArH-6), 7.28 (2H, d, J=8.7 Hz, ArH-3', 5'), 7.42 (2H, s, ArH-3", 5"), 7.73 (2H, d, J=8.7 Hz, ArH-2', 6'), 8.96 (1H, s, ArH-3), 10.07 (1H, s, NH).

Example 2

$N^1$-(4'-cyanophenyl)-5-(2',6'-dimethylphenoxy)-2,4-dinitroaniline (I-2)

The preparation method was the same as described in the preparation of I-1. The intermediate IV-1 (318.5 mg, 1 mmol) was allowed to react with 2,6-dimethylphenol (146.4 mg, 1.2 mmol) to obtain a product I-b (327 mg), yield 81%. $^1$H NMR (DMSO) δ ppm 2.06 (6H, s, 2×CH$_3$), 6.01 (1H, s, ArH-6), 7.09 (2H, d, J=8.7 Hz, ArH-3', 5'), 7.11 (1H, t, J=6.7 Hz, ArH-4"), 7.28 (2H, d, J=8.7 Hz, ArH-2', 6'), 7.69 (2H, d, J=6.7 Hz, ArH-3", 5"), 8.96 (1H, s, ArH-3), 10.07 (1H, s, NH).

Example 3

$N^1$-(4'-cyanophenyl)-2,4-dinitro-$N^5$-(2',4',6'-trimethylphenyl)-benzene-1,5-diamine(I-3)

The intermediate IV-1 (318 mg, 1 mmol) was dissolved in 2,4,6-trimethylaniline (1.5 mL) and allowed to react at 202° C. under microwave for 25 minutes. The resultant was poured into dilute hydrochloric acid aqueous solution, stirred for half an hour. The resulting precipitate was filtered, washed with water, dried, and separated on silica gel column to obtain a faint yellow solid compound I-3 (266 mg, 64%). Mass spectrum (EI-MS): m/z (%): 417[M$^+$, 100]; $^1$H NMR (DMSO-d$_6$) δ ppm 2.04 (6H, s, 2×CH$_3$), 2.24 (3H, s, 4"-CH$_3$), 5.56 (1H, s, ArH-6), 6.95 (2H, s, ArH-3", 5"), 7.21 (2H, d, J=8.7 Hz, ArH-3', 5'), 7.66 (2H, d, J=8.7 Hz, ArH-2', 6'), 9.02 (1H, s, ArH-3), 9.63 (2H, 2 NH).

Example 4

$N^1$-(4'-cyanophenyl)-2,4-dinitro-[$N^5$-acetoxy-$N^5$-(2',4',6'-trimethylphenyl)]benzene-1,5-diamine(I-4)

The intermediate IV-1 (64 mg, 0.2 mmol), 53 mg (0.3 mmol) 2,4,6-trimethylacetylaniline (34 mg, 0.3 mmol), potassium tert-butoxide were put in 3 mL DMSO, and allowed to react at 200° C. under microwave for 20 minutes. The resultant was poured into water, the pH value was adjusted to weak acidic. The resulting solid was pump filtered. The aqueous solution was extracted with ethyl acetate for three times. The organic phases were combined, and dried over magnesium sulfate. Ethyl acetate was removed by reduced pressure distillation. The crude was separated on silica gel plate (chloroform) to obtain 18 mg of faint yellow product. Yield 20%. $^1$H NMR (DMSO) δ ppm 1.91 (3H, s, COCH$_3$), 2.09 (6H, s, ArH-2", 6"), 2.27 (3H, s, ArH-4"), 6.53 (1H, s, ArH-6), 6.99 (2H, s, ArH-3", 5"), 7.55 (2H, d, J=8.4 Hz, ArH-2', 6'), 7.91 (2H, d, J=8.4 Hz, ArH-3', 5'), 8.71 (1H, s, ArH-3), 10.12 (1H, s, NH).

Example 5

4-(4'-Bromo-2',6'-dimethylphenoxy)-$N^2$-(4'-cyanophenyl)-5-nitrobenzene-1,2-diamine (I-5)

The compound I-1 (88 mg, 0.18 mmol) was dissolved in acetonitrile (2 mL). To the solution were added a small amount of Pd—C (5-10%) and triethylamine (0.06 mL), and dropped acetonitrile solution of formic acid (36 mg (95%) formic acid was dissolved in 1 mL acetonitrile) in ice bate with stir (about 5 minutes), then rapidly heated to reflux for 20 hours, separated on silica gel plate (chloroform was used as developing agent) to obtain 51 mg of product I-5. Yield 62%. $^1$H NMR (DMSO-d$_6$) δ ppm 2.07 (6H, s, 2×CH$_3$), 5.13 (2H, s, NH$_2$), 6.16 (1H, s, ArH-6), 6.82 (2H, d, J=8.4 Hz, ArH-3', 5'), 7.40 (2H, s, ArH-3", 5"), 7.55 (2H, d, J=8.4 Hz, ArH-2', 6'), 7.95 (1H, s, ArH-3), 8.45 (1H, s, NH).

Example 6

$N^1$-(4'-cyanophenyl)-5-(4'-cyano-2',6'-dimethylphenoxy)-2-nitroaniline (I-6)

The intermediate IV-4 (50 mg, 0.21 mmol) and 2,6-dimethyl-4-cyanophenol (37 mg, 0.25 mmol) were dissolved in dimethyl sulfoxide (2 mL). To the solution was added 58 mg (0.42 mmol) potassium carbonate. The system was sealed and allowed to react at 192° C. under microwave for 15 minutes. The resultant was poured into ice water to produce a precipitate. The solid was filtered and separated on silica gel column (petroleum ether/ethyl acetate) to obtain a faint yellow solid I-6 (32 mg), yield 46%. $^1$H NMR (CDCl$_3$) δ ppm 2.16 (6H, s, 2×CH$_3$), 6.15 (1H, q, J=9.2 & 2.4 Hz, ArH-4), 6.87 (1H, d, J=2.4 Hz, ArH-6), 7.31 (2H, d, J=8.4 Hz, ArH-3', 5'), 7.45 (2H, s, ArH-3", 5"), 7.66 (2H, d, J=8.4 Hz, ArH-2', 6'), 8.21 (1H, d, J=9.2 Hz, ArH-3), 9.75 (1H, s, NH).

Example 7

$N^1$-(4'-cyanophenyl)-5-(2',6'-dimethylphenoxy)-2-nitroaniline (I-7)

The intermediate IV-4 (50 mg, 0.18 mmol), 2,6-dimethylphenol (31 mg, 0.25 mmol) and potassium carbonate (58 mg, 0.42 mmol) were dissolved in DMSO (2 mL). The system was sealed and allowed to react at 192° C. under microwave for 15 minutes. The resultant was poured into ice water to produce a precipitate. The solid was filtered and separated on silica gel column (petroleum ether/ethyl acetate) to obtain a faint yellow solid I-7 (20 mg), yield 31%. $^1$H NMR (CDCl$_3$) δ ppm 2.12 (6H, s, 2×CH$_3$), 6.35 (1H, q, J=9.2 & 2.4 Hz, ArH-4), 6.73 (1H, d, J=2.4 Hz, ArH-6), 7.10 (3H, m, ArH-3", 4", 5"), 7.24 (2H, d, J=8.4 Hz, ArH-2', 6'), 7.59 (2H, d, J=8.4 Hz, ArH-3', 5'), 8.21 (1H, d, J=9.2 Hz, ArH-3), 9.76 (1H, s, NH).

Example 8

5-(4'-Bromo-2',6'-dimethylphenoxy)-N$^1$-(4'-cyanophenyl)benzene-1,2,4-triamine (I-8)

The compound I-1 (48.3 mg, 0.1 mmol) was dissolved 2 mL tetrahydrofuran. To the tetrehydrofuran solution was added methanol (1 mL) solution containing 7.13 mg (0.003 mmol) nickel chloride hexahydrate, added 18.9 mg (0.5 mmol) sodium boronhydride in batches in ice bath with stir, after 15 minutes, the resultant was poured into water, the pH value was adjusted to about 6, and then stirred for 15 minutes. The resulting solid was filtered and separated on silica gel plate (eluted with chloroform and methanol) to obtain 20 mg of brown solid product I-8, yield 47%. $^1$H NMR (DMSO-d$_6$) δ ppm 2.08 (6H, s, 2×CH$_3$), 4.28 (2H, s, NH$_2$-4), 4.91 (2H, s, NH$_2$-2), 5.70 (1H, s, ArH-3), 6.22 (1H, s, ArH-6), 6.43 (2H, d, J=8.8 Hz, ArH-2', 6'), 7.30 (2H, s, ArH-3", 5"), 7.38 (2H, d, J=8.8 Hz, ArH-3', 5'), 7.71 (1H, s, NH).

Example 9

N$^1$-(4'-Cyanophenyl)-5-(4'-cyano-2',6'-dimethylphenoxy)-2,4-dinitroaniline (I-9)

The preparation method was the same as described in the preparation of I-1. The intermediate IV-1 and 2,6-dimethyl-4-cyanophenol were allowed to react to obtain a faint yellow solid product I-9, yield 80%. Mass spectrum (EI-MS): m/z (%) 429 (M$^+$, 100); $^1$H NMR δ ppm 2.05 (6H, s, 2×CH$_3$), 5.93 (1H, s, ArH-3), 7.32 (2H, d, J=8.7 Hz, ArH-2', 6'), 7.42 (2H, s, ArH-3", 5"), 7.73 (2H, d, J=8.7 Hz, ArH-3', 5'), 8.96 (1H, s, ArH-6), 10.07 (1H, s, NH).

Example 10

N$^1$-(4'-cyanophenyl)-5-(4'-Cyano-2',6'-dimethylphenoxy)benzene-1,2,4-triamine (I-10)

The preparation method was the same as described in the preparation of I-8. The compound I-9 (93 mg, 0.217 mmol) was reduced to obtain a product I-10, 12 mg, yield 15.5%; $^1$H NMR (DMSO-d$_6$) δ ppm 2.08 (6H, s, 2×CH$_3$), 4.33 (2H, s, NH$_2$-4), 4.97 (2H, s, NH$_2$-2), 5.71 (1H, s, ArH-3), 6.23 (1H, s, ArH-6), 6.43 (2H, d, J=8.4 Hz, ArH-2', 6'), 7.38 (2H, d, J=8.4 Hz, ArH-3', 5'), 7.61 (2H, s, ArH-3", 5"), 7.71 (1H, s, NH).

Example 11

5-(4'-Cyano-2',6'-dimethylphenoxy)-N$^1$-(4'-cyanophenyl)-4-nitrobenzene-1,2-diamine (I-11)

The preparation method was as described in the preparation of I-5. The compound I-9 (37 mg, 0.086 mmol) was reduced to obtain a product I-11, 13 mg, yield 38%. $^1$H NMR (DMSO-d$_6$) δ ppm 2.07 (6H, s, 2×CH$_3$), 5.17 (2H, s, NH$_2$-2), 6.15 (1H, s, ArH-6), 6.81 (2H, d, J=8.8 Hz, ArH-2', 6'), 7.55 (2H, d, J=8.8 Hz, ArH-3', 5'), 7.71 (2H, s, ArH-3", 5"), 8.06 (1H, s, ArH-3), 8.45 (1H, s, NH).

Example 12

5-(4'-Bromo-2',6'-dimethylphenoxy)-N$^1$-(4'-cyanophenyl)-2-nitroaniline (I-12)

The preparation method was as described in the preparation of I-1. The compound IV-4 (100 mg, 0.36 mmol) and potassium 3-bromo-2,4-dimethylphenolate were coupled to obtain a product I-12, 147 mg, yield 93%. $^1$H NMR (CDCl$_3$) δ ppm 2.03 (6H, s, 2×CH$_3$), 6.19 (1H, q, J=9.3 & 2.5 Hz, ArH-6), 6.74 (1H, d, J=2.5 Hz, ArH-4), 7.21 (2H, d, J=8.8 Hz, ArH-2', 6'), 7.30 (2H, s, ArH-3", 5"), 7.57 (2H, d, J=8.8 Hz, ArH-3', 5'), 8.13 (1H, d, J=9.3 Hz, ArH-3), 9.69 (1H, s, NH).

Example 13

4-(4'-Bromo-2',6'-dimethylphenoxy)-N$^2$-(4'-cyanophenyl)benzene-1,2-diamine (I-13)

The preparation method was as described in the preparation of I-8. The compound I-12 (89 mg, 0.2 mmol) was reduced to obtain 21 mg product I-13, yield 26%. $^1$H NMR (DMSO-d$_6$) δ ppm 2.07 (6H, s, 2×CH$_3$), 4.55 (NH$_2$ active hydrogen), 6.34 (1H, s, ArH-6), 6.47 (1H, d, J=8.8 Hz, ArH-4), 6.65 (2H, d, J=8.8 Hz, ArH-2', 6'), 6.73 (1H, d, J=8.8 Hz, ArH-3), 7.34 (2H, s, ArH-3", 5"), 7.49 (2H, d, J=8.8 Hz, ArH-3', 5'), 8.08 (1H, s, NH)

Example 14

N$^1$-(4'-cyanophenyl)-5-(2',4',6'-trimethylphenoxy)-2,4-dinitroaniline (I-14)

The preparation method was as described in the preparation of I-1. The compound IV-1 (637 mg, 2 mmol) and 2,4,6-trimethylaniline (286 mg, 2.1 mmol) were allowed to react in the presence of anhydrous potassium carbonate (414 mg, 3 mmol) to obtain I-14, 580 mg, yield 70%, melting point 132° C. $^1$H NMR (DMSO-d$_6$) δ ppm 2.00 (6H, s, 2×CH$_3$-2",6"), 2.22 (3H, s, CH$_3$-4"), 5.92 (1H, s, ArH-6), 6.95 (2H, s, ArH-3", 5"), 7.27 (2H, d, J=8.7 Hz, ArH-2', 6'), 7.72 (2H, d, J=8.7 Hz, ArH-3', 5'), 8.95 (1H, s, ArH-3), 10.04 (1H, s, NH).

Example 15

5-(2',6'-dimethylphenoxy)-2,4-dinitro-N$^1$-(4'-methylphenyl)aniline (I-15)

The intermediate IV-3 that was not purified was directly added to 2,6-dimethylphenol (622 mg, 5.1 mmol) in an atmosphere of nitrogen. The mixture was heated to 125° C. and allowed to react for 2 hours. The resultant was poured into ice water and stirred for 20 minutes to precipitate a solid. The solid was pump filtered, washed with water, dried, and separated on silica gel column (eluant was petroleum ether: ethyl acetate) to obtain 884 mg of a faint yellow solid, yield 45%. $^1$H NMR (DMSO-d$_6$) δ ppm 2.06 (6H, s, 2×CH$_3$), 5.91 (1H, s, ArH-3), 6.7 (2H, d, J=8.12 Hz, ArH-2', 6'), 7.11 (1H, t, J=6.7 Hz, ArH-4"), 7.20 (2H, d, J=8.12 Hz, ArH-3', 5'), 7.69 (2H, d, J=6.7 Hz, ArH-3", 5"), 8.96 (1H, s, ArH-6), 9.70 (1H, s, NH).

Example 16

5-(4'-Bromo-2',6'-dimethylphenoxy)-2,4-dinitro-$N^1$-(4'-methylphenoxy)aniline (I-16)

The preparation method was as described in the preparation of I-1. The compound IV-2 (647 mg, 2 mmol) and 4-bromo-2,6-dimethylphenol (422 mg, 2.1 mmol) were allowed to react to obtain I-16, 517 mg, faint yellow solid, yield 53%. $^1$H NMR (CDCl$_3$) δ ppm 2.07 (6H, s, 2×CH$_3$), 3.78 (3H, s, OCH$_3$), 5.91 (1H, s, ArH-3), 6.75 (2H, d, J=8.96 Hz, ArH-2', 6'), 6.89 (2H, d, J=8.96 Hz, ArH-3', 5'), 7.34 (2H, s, ArH-3", 5"), 9.17 (1H, s, ArH-6), 9.68 (1H, s, NH).

Example 17

$N^1$-(4'-cyanophenyl)-5-(2',6'-dimethylphenoxy)-3-nitroaniline (I-17)

The intermediate IV-5 (43 mg, 0.15 mmol), 2,6-dimethylphenol (49 mg, 0.60 mmol) and potassium carbonate (42 mg, 0.3 mmol) were placed in 2 mL DMSO, allowed to react at 200° C. under microwave for 30 minutes. The resultant was poured into water. The pH value was adjusted to weak acidity. The resulting solid was filtered, washed with water, dried, and separated on silica gel column (petroleum ether: ethyl acetate) to obtain 5 mg of a faint yellow solid, yield 10%. $^1$H NMR (CDCl$_3$) δ ppm 2.18 (6H, s, 2×CH$_3$), 6.31 (1H, s, ArH-6), 6.69 (2H, d, J=4.2 Hz, ArH-3", 5"), 6.88 (1H, t, J=4.2 Hz, ArH-4"), 7.08 (2H, d, J=8.8 Hz, ArH-2', 6'), 7.11 (2H, s, ArH-2, 4), 7.54 (2H, d, J=8.8 Hz, ArH-3', 5').

Example 18

$N^1$-(4'-Cyanophenyl)-5-(4'-propenylcyano-2',6'-dimethylphenoxy)-2,4-dinitroanine (I-18)

The compound I-1 (48.3 mg, 0.1 mmol), acrylonitrile (53 mg, 1 mmol), palladium acetate (4.5 mg, 0.02 mmol) and triphenyl phosphine (26 mg, 0.1 mmol) were allowed to react in triethylamine under microwave for 30 minutes. The resultant was poured into water, extracted with ethyl acetate. The extract was dried over magnesium sulfate. The solvent was removed by reduced pressure distillation. The crude product was separated on silica gel plate (dichloromethane) to obtain 6 mg of a yellow solid product I-18, yield 13.2%. $^1$H NMR (CDCl$_3$) δ ppm 2.18 (6H, s, 2×CH$_3$), 5.86 (1H, d, J=16.4 Hz, olefinic hydrogen adjacent to cyano), 6.26 (1H, s, ArH-6), 7.12 (2H, d, J=8.8 Hz, ArH-2', 6'), 7.21 (2H, s, ArH-3", 5"), 7.32 (1H, d, J=16.4 Hz, olefinic hydrogen adjacent to phenyl ring), 7.55 (2H, d, J=8.8 Hz, ArH-3', 5'), 9.19 (1H, s, ArH-3), 9.97 (1H, s, NH).

Example 19

$N^1$-(4'-Cyanophenyl)-5-(4'-propenylcyano-2',6'-dimethylphenoxy)-4-nitrobenzene-1,2-diamine(I-19)

The compound I-5 (45 mg, 0.1 mmol), acrylonitrile (53 mg, 1 mmol), palladium acetate (4.5 mg, 0.02 mmol) and triphenyl phosphine (26 mg, 0.1 mmol) were refluxed in an atmosphere of nitrogen in triethylamine (4 mL) and DMF (2 mL) for 25 hours. The resultant was poured into water. The pH value was adjusted to weak acidity. The solid was pump filtered, washed with water, dried, and separated on silica gel plate (petroleum ether: ethyl acetate) to obtain 10 mg of a solid product I-19, yield 23%. Mass spectrum (EI-MS) m/z (%) 426 (M+H$^+$,100); $^1$H NMR (CDCl$_3$) δ ppm 2.18 (6H, s, 2×CH$_3$), 3.55 (2H, s, NH$_2$), 5.82 (1H, d, J=16.8 Hz, olefinic hydrogen on the same carbon with cyano group), 6.31 (1H, s, ArH-6), 6.76 (2H, d, J=8.68 Hz, ArH-2', 6'), 7.20 (2H, s, ArH-3", 5"), 7.32 (1H, d, J=16.8 Hz, olefinic hydrogen not on the same carbon with cyano group), 7.47 (2H, d, J=8.68 Hz, ArH-3', 5'), 7.63 (1H, s, ArH-3).

Example 20

$N^1$-(4'-Cyanophenyl)-5-{2',6'-dimethyl-4'-[2"-(5"-formylfuran)]phenoxy}-2,4-dinitroaniline (I-20)

The intermediate V-I (96.6 mg, 0.2 mmol), 5-formyl-2-furyl borate (56 mg, 0.4 mmol), palladium acetate (4.5 mg, 0.02 mmol), triphenyl phosphine (15.7 mg, 0.06 mmol) and cesium carbonate (197 mg, 0.6 mmol) were allowed to react at 80° C. in 3 ML DMF under microwave for 20 minutes. The resultant was poured into water. The pH value was adjusted to weak acidity. The solid was filtered, washed with water, dried, and separated on silica gel plate (petroleum ether: chloroform) to obtain 50 mg of a faint green solid product I-20, yield 50%. Melting point: 198° C. $^1$H NMR (CDCl$_3$) δ ppm 2.18 (6H, s, 2×CH$_3$), 6.28 (1H, s, ArH-6), 6.85 (1H, d, J=3.9 Hz, hydrogen adjacent to phenyl ring on furan ring), 7.10 (2H, d, J=8.8 Hz, ArH-2', 6'), 7.36 (1H, d, J=3.9 Hz, hydrogen adjacent to formyl group on furan ring), 7.50 (2H, d, J=8.8 Hz, ArH-3', 5'), 7.59 (2H, s, ArH-3", 5"), 9.20 (1H, s, ArH-3), 9.67 (1H, s, CHO), 9.94 (1H, s, NH).

Example 21

Assay of Anti-HIV Activity (H9 Cell Model)

Reference document (J. Med. Chem. 2004, 47, 756-760). Lymphocyte H9 was cultured at 37° C. in culture medium 1640 and 5% CO$_2$. The tested compound was initially dissolved in DMSO, and then diluted with culture medium to conventional screening concentration: 100, 20, 4, 0.8 μg/mL. The cultured H9 cells were divided into two parts, wherein one of the parts was infected with HIV virus (IIIB) (m.i.o. 0.1-0.01 infectious Units/cell), which was used for assaying activity. The other part of the cells was not added with viruses but only with culture medium, which was used for assaying toxicity. The two parts of the cells were cultured under completely identical conditions (37° C., 5% CO$_2$) for 4 hours, washed with fresh culture medium for three times, and then were added respectively to the prepared tested samples of different concentrations or to culture medium (the latter was positive infection control or negative drug control), and meanwhile AZT was used as positive drug control. All these cells were cultured at 37° C. in 5% CO$_2$ for 4 days. In the fourth day, the cell membranes of the cells infected by viruses were removed, and the cytosol was tested by P24 antigen ELISA method to assay the activity of the sample, expressed using EC$_{50}$. EC$_{50}$ was an effective concentration when virus replication was inhibited by 50%. The part of the cells without viruses added were tested by the method of counting cells to assay the toxicity of the sample, expressed using CC$_{50}$. CC$_{50}$ was a concentration when growth cells were killed by 50%.

Example 22

Assay of Anti-HIV Activity (MT-2 Cell Model)

Reference documents (Jiang, S., et al. Antimicrob. Agents Chemother. 2004, 48, 4349-4359). In 96 wells culture plate, 50 μl of different concentrations of compound solutions were mixed with HIV-1$_{IIIB}$ virus strains (100 TCID$_{50}$) in the same volume, incubated at 37° C. for 30 minutes, added with 100 μl TM-2 cell (1×10$^5$/mL, RPIM 1640 culture medium containing 10% serum), mixed uniformly, and incubated at 37° C. overnight. In the second day, 150 μl supernatant was sucked off and supplemented with fresh culture medium in the same volume, the compound solutions were incubated continuously at 37° C. for 3 days, and the cell pathology effect (CPE) was recorded in the fourth day. Then 100 μl cultured supernatant was sucked up to determine p24 antigen therein with 5% Triton X-100 lytic virus particles by using ELISA method. Briefly, HIVIG (2 μg/ml) was used to encapsulate enzyme standard plate, sealed with 1% fat-free milk, and then added with virus lytic solution, incubated at 37° C. for 60 minutes. After the plate was washed completely, anti-p24 monoclonal antibody-183-12H-5C, goat anti-mouse antibody labeled with biotin and horse radish peroxidase labeled with avidin were added. Then the compounds were developed with TMB, and the light density was tested at 450 nm. The virus inhibition concentration of 50% (EC$_{50}$) of the compounds was calculated by using CalcuSyn software.

Example 23

Cytotoxicity Test of Compound

Reference documents (Jiang, S., et al. Antimicrob. Agents Chemother. 2004, 48, 4349-4359). In 96 wells culture plate, 50 μl of different concentrations of compound solutions were mixed with PBS in the same volume, incubated at 37° C. for 30 minutes, added with 100 μL TM-2 (or H9) cell (1×10$^5$/mL, RPIM 1640 culture medium containing 10% serum), mixed uniformly, and incubated at 37° C. overnight. In the second day, 150 μL supernatant was sucked off and supplemented with fresh culture medium in the same volume, the compound solutions were incubated continuously at 37° C. for 3 days, and added in the fourth day with 50 μL fresh XTT solution (1 mg/mL) containing PMS, after 4 hours later, the light density of the compounds was determined at 450 nm The cytotoxicity concentration of 50% (CC$_{50}$) of the compounds was calculated by using CalcuSyn software.

Partial biological assay results were shown in Table 1.

TABLE 1

Test data of anti-HIV activity (H9 and MT-2 cells)

| Compound No. | cell line | CC$_{50}$ (μg/mL) | EC$_{50}$ (μg/mL) | SI* (CC$_{50}$/EC$_{50}$) |
|---|---|---|---|---|
| I-1 | H9 | >25 | 0.11 | >234 |
| | MT-2 | >100 | 0.14 | >714 |
| I-2 | H9 | >25 | 0.22 | >113 |
| | MT-2 | >100 | 3.71 | >27 |
| I-3 | H9 | >25 | 0.055 | >455 |
| | MT-2 | >100 | 0.18 | >556 |
| I-4 | H9 | >25 | 1.77 | >14.15 |
| | MT-2 | 61.21 | 2.61 | 23.45 |
| I-5 | H9 | >25 | <0.025 | >1000 |
| | MT-2 | 61.08 | <0.02 | >3054 |
| I-6 | H9 | >25 | 0.08 | >312 |
| | MT-2 | 56.53 | 6.63 | 8.53 |
| I-7 | H9 | >25 | 0.76 | >33 |
| | MT-2 | >100 | 1.18 | >85 |
| I-8 | H9 | 16.25 | 0.068 | 239 |
| | MT-2 | 17.18 | 0.13 | 132 |
| I-10 | H9 | 20.5 | <0.025 | >820 |
| | MT-2 | 19.40 | 0.008 | 2425 |

TABLE 1-continued

Test data of anti-HIV activity (H9 and MT-2 cells)

| Compound No. | cell line | CC$_{50}$ (μg/mL) | EC$_{50}$ (μg/mL) | SI* (CC$_{50}$/EC$_{50}$) |
|---|---|---|---|---|
| I-11 | H9 | >25 | <0.025 | >1000 |
| | MT-2 | 61.29 | 0.013 | 4715 |
| I-13 | H9 | 17.2 | 0.134 | 128 |
| | MT-2 | 14.50 | 0.16 | 91 |
| I-14 | H9 | >25 | 0.144 | >174 |
| | MT-2 | 28.76 | 0.70 | 41.09 |

*SI: the selectivity index of compound, being ratio of cytotoxicity CC$_{50}$ value to activity EC$_{50}$ value.

The results have shown that the compounds of formula I according to the present invention are anti-HIV active compounds having new skeletal structure. Since this class of compounds exhibit good molecular flexibility, the compounds of the present invention may have strong inhibition activity to HIV tolerant virus strains in large extent and may be developed as new anti-HIV drugs having novel structure.

The invention claimed is:

1. Compound of formula (I) or a pharmaceutically acceptable salt thereof:

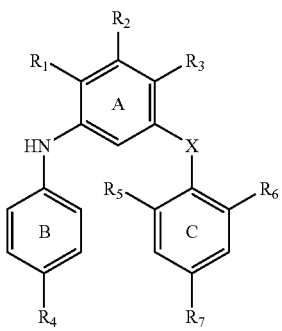

I wherein,
R$_1$, R$_2$ and R$_3$ are each independently —H, halogen, —NO$_2$, —NH$_2$, —NHR, —N(R)$_2$, —CN, —OH, C$_{1-6}$alkyl, C$_{1-6}$alkoxy, —CF$_3$, —COOH, —SO$_3$H, —CONH$_2$, —CONHR' or —COOR',
or, R$_1$ and R$_2$ or R$_2$ and R$_3$ can form together —OCH$_2$O—;
R$_4$ is —CN, —CH=CH$_2$, —C≡CH, C$_{1-6}$alkyl, C$_{1-6}$alkoxy, —CF$_3$, halogen, —NH$_2$, —OH, —COOH, —SO$_3$H, —C≡CR' or —CH=CHR';
R$_5$ and R$_6$ are each independently halogen, C$_{1-6}$alkyl, C$_{1-6}$alkoxy, —CF$_3$, —NH$_2$, —OH, —COOH, —SO$_3$H or COOR';
R$_7$ is —CN, —HC=CH—CN, halogen, C$_{1-6}$alkyl, C$_{1-6}$alkoxy, —NH$_2$, —OH, —NO$_2$, —CF$_3$, —CH=CH$_2$, —C≡CR', —CH=CHR', —CH=CHCOR', —CHO or 5-membered heteroaryl containing 1-3 heteroatoms selected from N, O and S, and optionally having on the ring structure thereof aldehyde, ketone, cyano, α, β-unsaturated cyano, alkenyl, alkynyl, aldehyde or ketone group substitution;
R' is H or C$_{1-6}$alkyl radical;
X: —NH—, —O—, —S—, —CH$_2$—, —CO—, —CHOH—, —CHOR—, —NR— or —NCOR—; and
R is C$_{1-4}$alkyl radical.

2. The compound of claim 1, wherein X is —O—.

3. The compound of claim 1, wherein the compound of formula (I) has following formula (Ia):

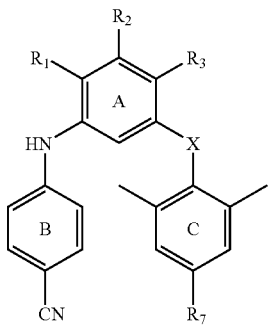

wherein, $R_1$ and $R_3$ are each independently —$NO_2$, —$NH_2$, halogen, —OH, —CN or —$N(R)_2$;

$R_2$—H;

$R_7$ is —CN, —HC═CH—CN, halogen, —$CH_3$, —$OCH_3$, —$NH_2$, —OH, —$NO_2$, —$CF_3$, —CH═$CH_2$, —C≡CH, —C≡CR', —CH═CHR', —CH═CHCOR', —CHO or 5-membered heteroaryl containing 1-3 heteroatoms selected from N, O and S, and optionally having on the ring structure thereof aldehyde, ketone, cyano, α, β-unsaturated cyano, alkenyl, alkynyl, aldehyde or ketone group substitution;

R' is H or $C_{1-6}$alkyl radical;

X is —O—, —NH— or —NCOR—; and

R is $C_{1-4}$alkyl radical.

4. The compound of claim 1, wherein the compound of formula (I) has following formula (Ia):

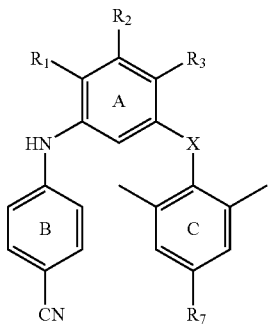

$R_1$ is —$NO_2$, —$NH_2$, halogen, —OH, —CN or —$N(R)_2$;

$R_2$ and $R_3$ are —H;

$R_7$ is —CN, —HC═CH—CN, halogen, —$CH_3$, —$OCH_3$, —$NH_2$, —OH, —$NO_2$, —$CF_3$, —CH═$CH_2$, —C≡CH, —C≡CR', —CH═CHR', —CH═CHCOR', —CHO or 5-membered heteroaryl containing 1-3 heteroatoms selected from N, O and S, and optionally having on the ring structure thereof aldehyde, ketone, cyano, α, β-unsaturated cyano, alkenyl, alkynyl, aldehyde or ketone group substitution;

R' is H or $C_{1-6}$alkyl radical;

X is —O—, —NH— or —NCOR—; and

R is $C_m$alkyl radical.

5. The compound of claim 1, wherein the compound of formula (I) has following formula (Ia):

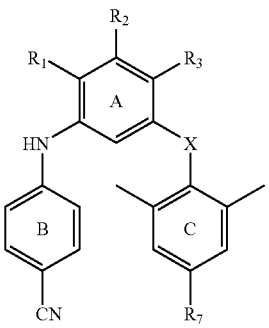

$R_2$ is —$NO_2$, —$NH_2$, halogen, —OH, —CN or —$N(R)_2$;

$R_1$ and $R_3$ are —H;

$R_7$ is —CN, —HC═CH—CN, halogen, —$CH_3$, —$OCH_3$, —$NH_2$, —OH, —$NO_2$, —$CF_3$, —CH═$CH_2$, —C≡CH, —C≡CR', —CH═CHR', —CH═CHCOR', —CHO or 5-membered heteroaryl containing 1-3 heteroatoms selected from N, O and S, and optionally having on the ring structure thereof aldehyde, ketone, cyano, α, β-unsaturated cyano, alkenyl, alkynyl, aldehyde or ketone group substitution;

R' is H or $C_{1-6}$alkyl radical;

X is —O—, —NH— or —NCOR—; and

R is $C_{1-4}$alkyl radical.

6. (Previously rresented) The compound of claim 1, wherein the compound of formula (I) has following formula (Ia):

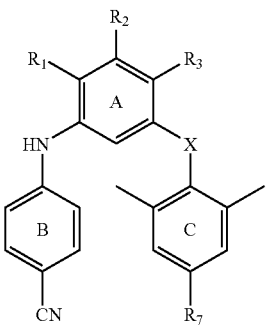

$R_3$ is —$NO_2$, —$NH_2$, halogen, —OH, —CN or —$N(R)_2$;

$R_1$ and $R_2$ are —H;

$R_7$ is —CN, —HC═CH—CN, halogen, —$CH_3$, —$OCH_3$, —$NH_2$, —OH, —$NO_2$, —$CF_3$, —CH═$CH_2$, —C≡CH, —C≡CR', —CH═CHR', —CH═CHCOR', —CHO or 5-membered heteroaryl containing 1-3 heteroatoms selected from N, O and S, and optionally having on the ring structure thereof aldehyde, ketone, cyano, α, β-unsaturated cyano, alkenyl, alkynyl, aldehyde or ketone group substitution;

R' is H or $C_{1-6}$alkyl radical;

X is —O—, —NH— or —NCOR—; and

R is $C_{1-4}$alkyl radical.

7. The compound of claim 1 selected from:

$N^1$-(4'-cyanophenyl)-5-(2',6'-dimethyl-4'-bromophenoxy)-2,4-dinitroaniline;

$N^1$-(4'-cyanophenyl)-5-(2',6'-dimethylphenoxy)-2,4-dinitroaniline;

$N^1$-(4'-cyanophenyl)-2,4-dinitro-$N^5$-(2',4',6'-trimethylphenyl)benzene-1,5-diamine;

$N^1$-(4'-cyanophenyl)-2,4-dinitro-[$N^5$-acetoxy-$N^5$-(2',4',6'-trimethylphenyl)]benzene-1,5-diamine;

4-(4'-bromo-2',6'-dimethylphenoxy)-$N^2$-(4'-cyanophenyl)-5-nitrobenzene-1,2-diamine;

$N^1$-(4'-cyanophenyl)-5-(4'-cyano-2',6'-dimethylphenoxy)-2-nitoaniline;

$N^1$-(4'-cyanophenyl)-5-(2',6'-dimethylphenoxy)-2-nitroaniline;

5-(4'-bromo-2',6'-dimethylphenoxy)-$N^1$-(4'-cyanophenyl)benzene-1,2,4-triamine;

$N^1$-(4'-cyanophenyl)-5-(4'-cyano-2',6'-dimethylphenoxy)-2,4-dinitroaniline;

$N^1$-(4'-cyanophenyl)-5-(4'-cyano-2',6'-dimethylphenoxy)benzene-1,2,4-triamine;

5-(4'-cyano-2',6'-dimethylphenoxy)-$N^1$-(4'-cyanophenyl)-4-nitrobenzene-1,2-diamine;

5-(4'-bromo-2',6'-dimethylphenoxy)-$N^1$-(4'-cyanophenyl)-2-nitroaniline;

4-(4'-bromo-2',6'-dimethylphenoxy)-$N^2$-(4'-cyanophenyl)benzene-1,2-diamine;

$N^1$-(4'-cyanophenyl)-5-(2',4'6'-trimethylphenoxy)-2,4-dinitroaniline;

5-(2',6'-dimethylphenoxy)-2,4-dinitro-$N^1$-(4'-methylphenyl) aniline;

5-(4'-bromo-2',6'-dimethylphenoxy)-2,4-dinitro-$N^1$-(4'-methylphenoxy)aniline;

$N^1$-(4'-cyanophenyl)-5-(2',6'-dimethylphenoxy)-3-nitroaniline;

$N^1$-(4'-cyanophenyl)-5-(4'-propenylcyano-2',6'-dimethylphenoxy)-2,4-dinitroaniline;

$N^1$-(4'-cyanophenyl)-5-(4'-propenylcyano-2',6'-dimethylphenoxy)-4-nitrobenzene-1,2-diamine; and $N^1$-(4'-Cyanophenyl)-5-{2',6'-dimethyl-4'-[2''-(5''-formylfuran)]phenoxy}-2,4-dinitroaniline.

8. A process for preparing a compound as claimed in claim 1:

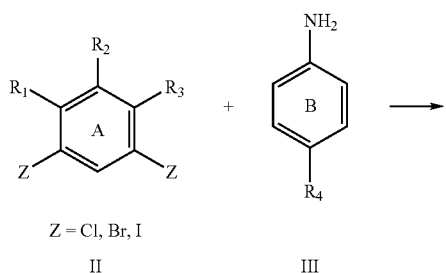

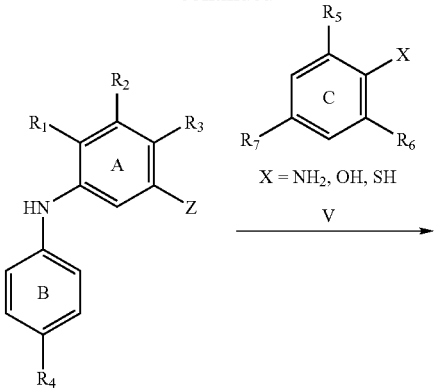

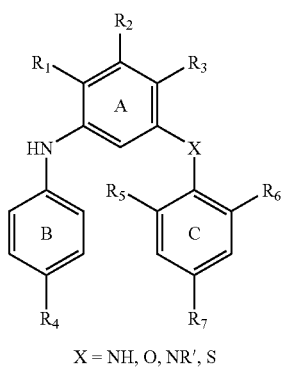

wherein $R_1$-$R_7$ and X are as defined in the formula (I),
comprising: reacting substituted m-dihalobenzene of formula (II) with p-substituted anilines in the presence of a strong base to form N-aryl substituted aniline of formula (IV); coupling the intermediate of folinula (IV) and multi-substituted phenols or anilines, or heating in the presence of Pd catalyst or coupling under microwave condition to produce m-di(aromatic)-polysubstituted anilines of formula (I).

9. A pharmaceutical composition comprising a compound as claimed in claim 1 or a pharmaceutically acceptable salt thereof and one or more pharmaceutically acceptable carriers or excipients.

10. A method of inhibiting HIV virus replication in a patient comprising administering to the patient an amount of a compound of claim 1 or a pharmaceutically acceptable salt thereof effective to inhibit HIV replication in a patient.

11. The method of claim 10, wherein the compound is administered to the patient at from 0.01 to 100 mg/kg body weight/day.

* * * * *

UNITED STATES PATENT AND TRADEMARK OFFICE
CERTIFICATE OF CORRECTION

PATENT NO.        : 8,309,602 B2                                    Page 1 of 1
APPLICATION NO.   : 12/682513
DATED             : November 13, 2012
INVENTOR(S)       : Lan Xie et al.

It is certified that error appears in the above-identified patent and that said Letters Patent is hereby corrected as shown below:

Column 19, Line 65, Claim 4, delete "$C_m$alkyl" and insert -- $C_{1-4}$alkyl --

Column 20, Line 30, Claim 6, delete "(Previously rresented) The" and insert -- The --

Column 21, Line 17, Claim 7, delete "b enzene" and insert -- benzene --

Column 22, Line 40, Claim 8, delete "folinula" and insert -- formula --

Signed and Sealed this
Fifth Day of February, 2013

Teresa Stanek Rea
*Acting Director of the United States Patent and Trademark Office*